United States Patent [19]

Payton

[11] 4,217,893
[45] Aug. 19, 1980

[54] ABOVE-THE-KNEE CAST

[76] Inventor: Hugh W. Payton, 416 Jupiter St., Washington Court House, Ohio 43160

[21] Appl. No.: 49,682

[22] Filed: Jun. 18, 1979

Related U.S. Application Data

[63] Continuation of Ser. No. 820,558, Aug. 1, 1977, abandoned.

[51] Int. Cl.³ .............................................. A61F 5/04
[52] U.S. Cl. ................................... 128/89 R; 128/165
[58] Field of Search .................... 128/89 R, 87 R, 90, 128/91 R, 80 R, 165

[56] References Cited

U.S. PATENT DOCUMENTS

| 3,701,349 | 10/1972 | Larson | 128/89 R X |
| 3,800,789 | 4/1974 | Schloss | 128/90 |
| 3,955,565 | 5/1976 | Johnson, Jr. | 128/89 R |

FOREIGN PATENT DOCUMENTS 76077  4/1916  Austria .................................. 128/89 R Primary Examiner—John D. Yasko
Attorney, Agent, or Firm—Biebel, French & Nauman

[57] ABSTRACT

A non-weight bearing above-the-knee cast comprises a rigid posterior shell extending from the mid-thigh over the back of the knee, throughout the lower leg and under the foot with the knee and the foot being held in positions of physiological rest with pliable sides and confining elements spaced throughout the entire length to retain the knee, leg and foot in immobilized position.

13 Claims, 12 Drawing Figures

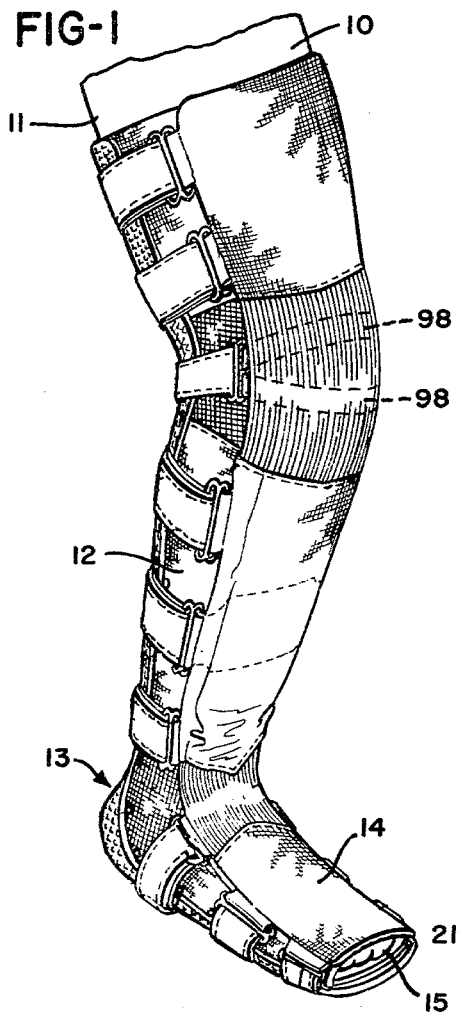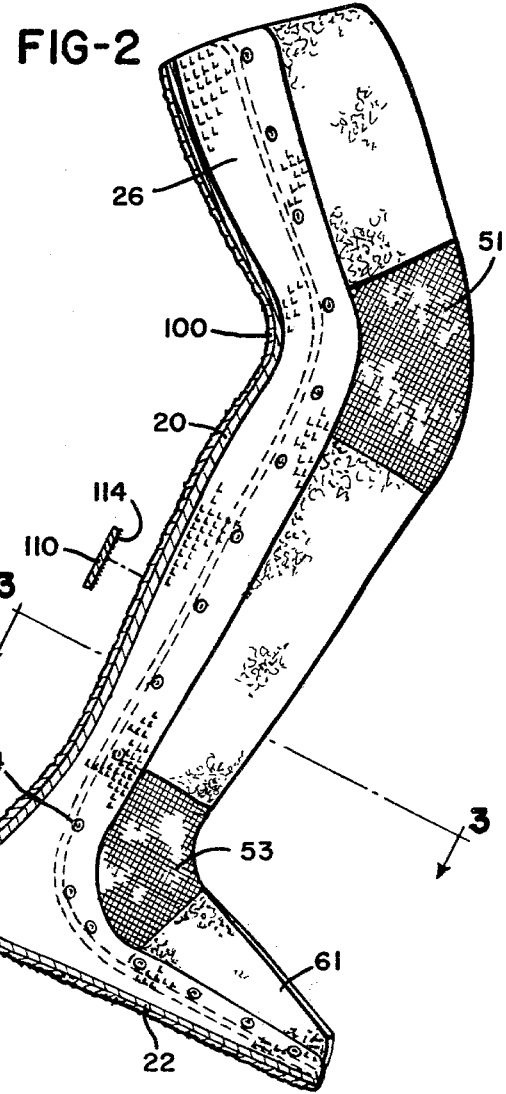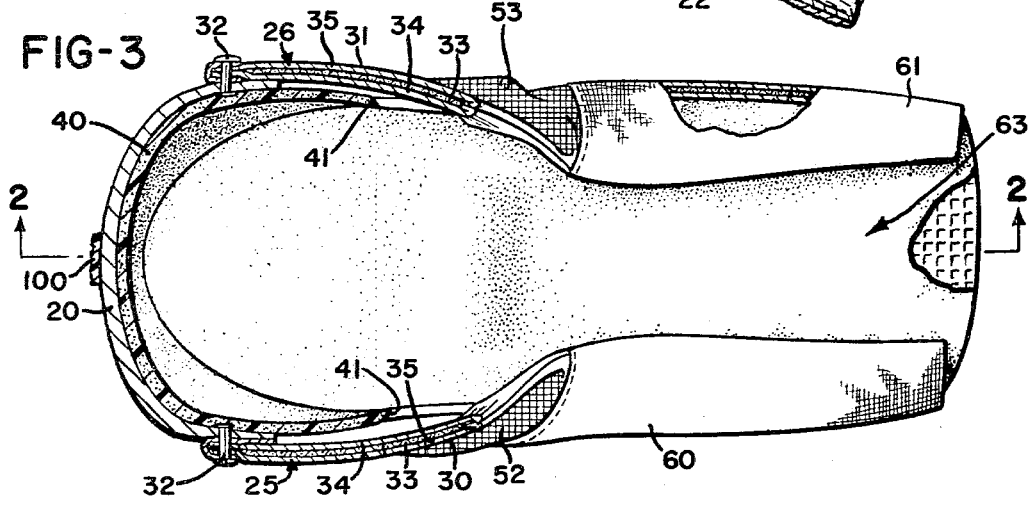

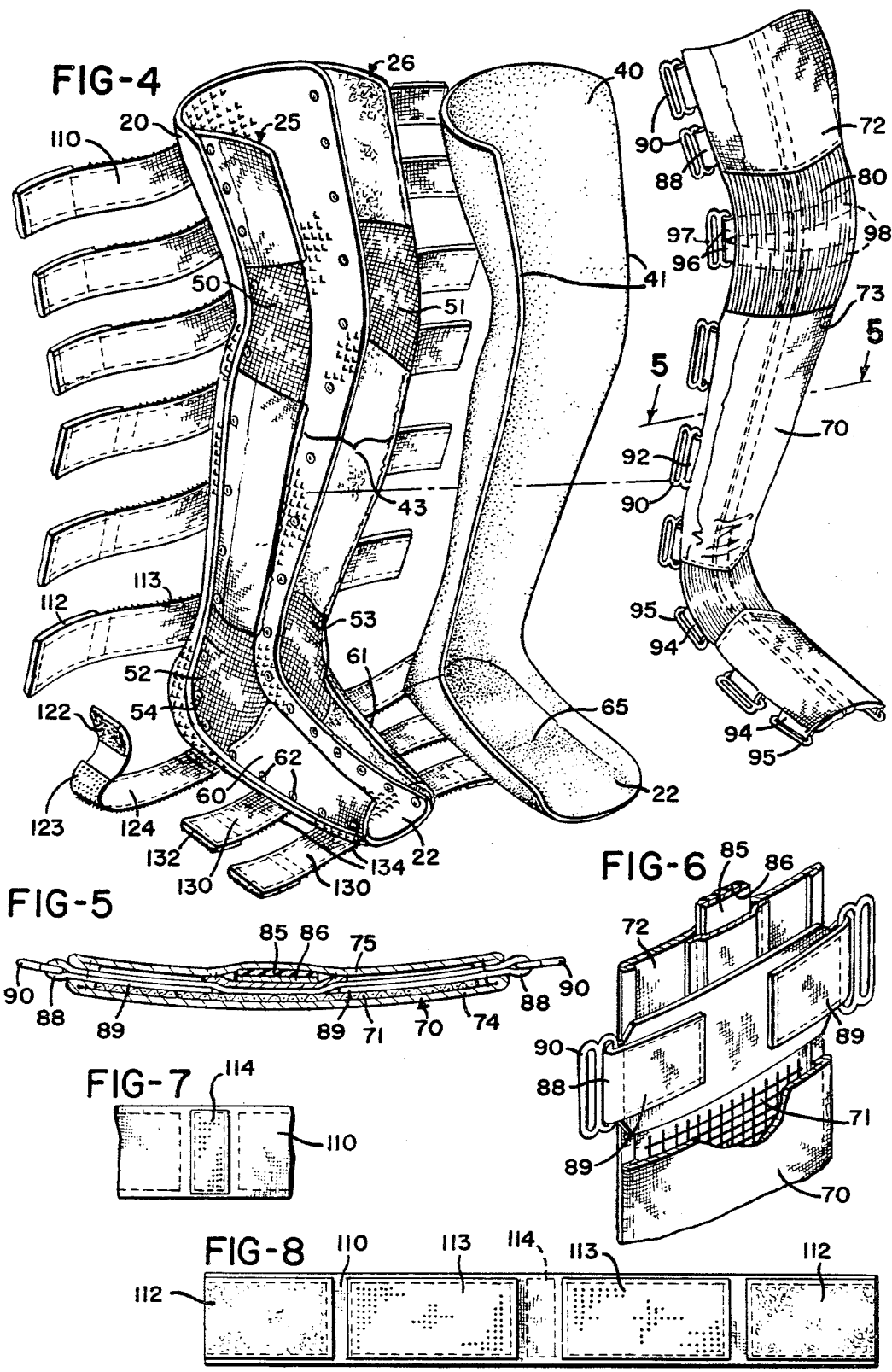

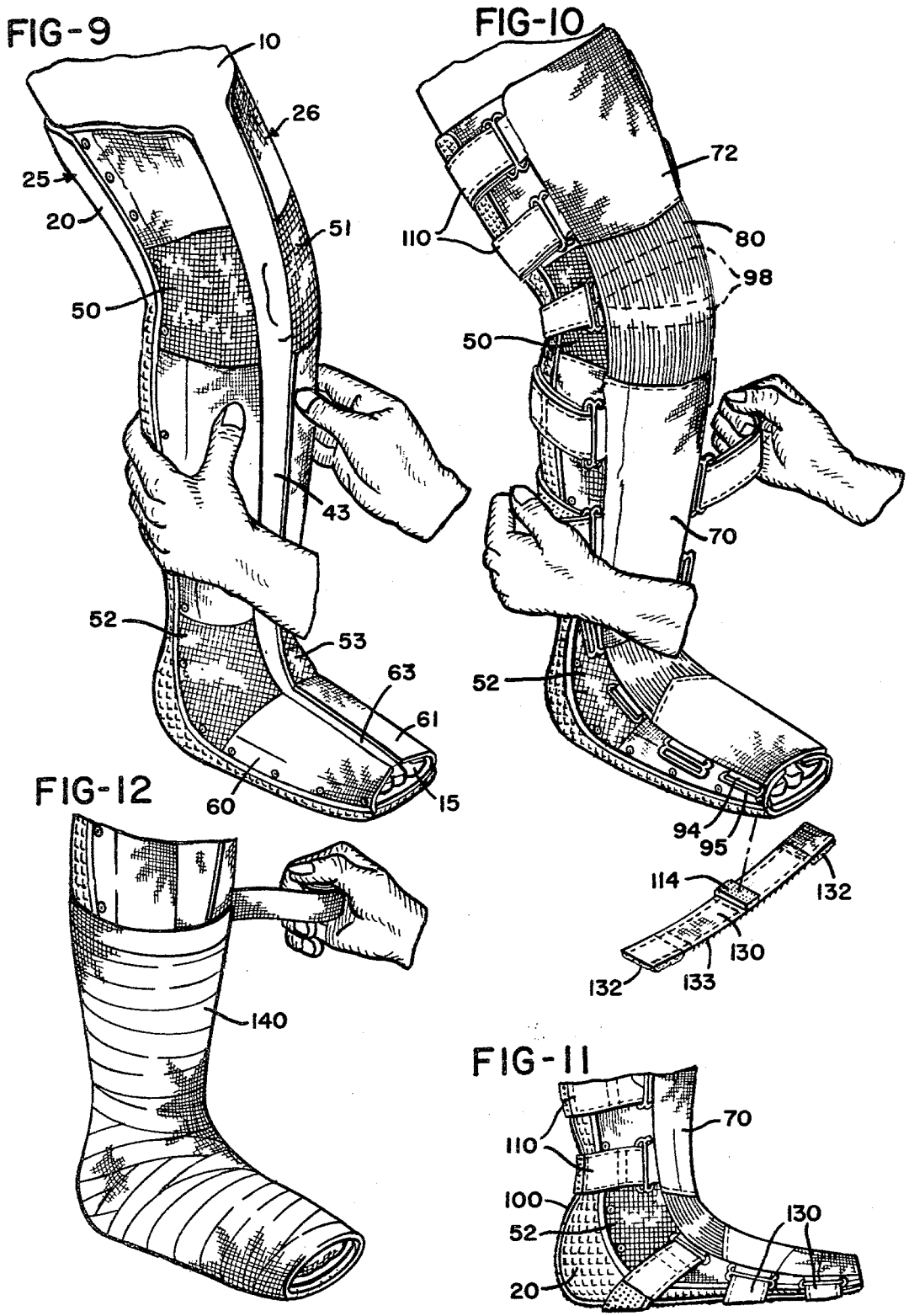

ABOVE-THE-KNEE CAST

This is a continuation of application Ser. No. 820,558 filed Aug. 1, 1977, now abandoned.

BACKGROUND OF THE INVENTION

Fractures of the knee, tibia or fibula, strains or torn ligaments in the knee, ankle or in the foot are usually accompanied by considerable pain and rapid swelling in the area affected. In some cases it is necessary to "set" a fracture, while in other cases, notably a fracture of the fibula, the physician usually does not perform any setting operation. In both situations the important factor is to immobilize the entire leg, knee, ankle and foot, after which the healing of the situation occurs by natural processes.

In my co-pending application Ser. No. 691,447, filed June 1, 1976 (now U.S. Pat. No. 4,057,056 issued Nov. 8, 1977) a walking cast is disclosed which extends from the mid-calf around the ankle and under the foot together with a detachable rocker shaped foot member which allows the wearer to walk and which is also readily removable when the patient is at rest or desires to take a bath.

SUMMARY OF THE INVENTION

The present invention utilizes some of the features of the above-identified application for reasons and with advantages similar to those set forth therein, but is intended to be a non-weight supporting cast and to extend from the mid-thigh, over the entire length of the lower leg and the foot, and to retain the thigh and leg as well as the foot and the lower leg in a predetermined position of physiological rest. The cast is intended to be supplied in different sizes to be adaptable to persons of different heights and weight and to be disposed of after a single use.

BRIEF DESCRIPTION OF THE DRAWINGS

Referring to the drawings which show preferred embodiments of the invention:

FIG. 1 is a perspective view of the cast in place on the leg, ankle and foot of a patient;

FIG. 2 is a vertical section through the cast on line 2—2 of FIG. 3;

FIG. 3 is a horizontal section on line 3—3 of FIG. 2;

FIG. 4 is an exploded view of the cast of FIG. 1 showing the shell and attached side members, the plastic liner, the tongue;

FIG. 5 is a horizontal section through the tongue on the line 5—5 of FIG. 4;

FIG. 6 is a partial perspective view of the tongue with parts being broken away;

FIG. 7 is a fragmentary view of the inner face of one of the fastening straps and showing a male Velcro section;

FIG. 8 is a broken view of the outer face of a strap showing the spaced location of adjacent male and female Velcro sections;

FIG. 9 is a perspective view showing an initial step in applying the cast to a patient's leg and shaping the same to the contours of the calf and foot;

FIG. 10 shows a later step in which the tongue is placed in position on the anterior portion of the leg, ankle and upper portion of the foot with the straps threaded through the D-rings preparatory to being fastened;

FIG. 11 is a side view showing the final position of the cast in place; and

FIG. 12 is a view of a modified arrangement in which a conventional plaster wrapping is applied over the shell.

DESCRIPTION OF THE PREFERRED EMBODIMENT

Referring to the embodiment shown in FIGS. 1 through 12, the patient's leg is shown at 10 with the anterior portion 11 of the upper leg, the lower leg 12, the ankle 13 and the foot 14 and the toes 15 enclosed in the cast of the present invention. The first component of the cast is a rigid non-bendable plastic shell 20 extending from the mid-thigh, over the calf, having a heel portion 21 and a bottom portion 22 on which the foot is supported. A suitable material for this purpose is a polyethylene, polypropylene, etc., plastic. The main shell has side extensions 25, 26 which are pliable to some extent so that when the cast is applied, these side extensions may be molded by manual pressure to conform to the leg size of the individual patient. One of the critical areas is the rear of the heel where protection is afforded for the Achilles tendon and where by the geometry of the shell the maximum bending moments are concentrated, it being important that the shell be completely rigid and non-bending in this area.

It is important that the leg be supported in a position of physiological rest at an angle of approximately 15° to 20° to the thigh and with the foot at an angle of approximately 90° to the long axis of the lower leg and with no inversion or eversion.

Fabric side members 30, 31 are secured to the shell 20 by means of a series of rivets 32, the side members 30, 31 overlying the lateral portions of the leg and being moldable over the anterior portion of the upper leg and calf and having an interior of woven wire 33 such as that known as hardware cloth. The inner face of the side members is covered by a soft fabric 34 which will not abrade the skin with which it comes in contact, while the outer face of the side members is likewise cloth covered but with a cloth 35 which has water resistant properties and which is capable of being washed. The side members can be manually molded to conform to the shape of the patient's leg and will tend to retain their molded shape.

A liner 40 of plastic foam material is received against the inner face of shell 20 and extends forwardly beyond the shell with skived edges as shown at 41, but terminating short of the side members 30, 31. Thus side members 30, 31 do not overlap but are separated by a gap 43 on the anterior face of the lower leg. The reason for the gap is to allow the cast to conform to and fit the shape of the actual leg to which it is applied, the size and shape of which are subject to considerable normal variation as well as to abnormal variations resulting from the injury. The plastic liner 40 continues over the heel 21 and the foot portion 22 so that the entire lower extremity of the patient rests in contact with the plastic foam material.

In the knee and ankle areas the side members 30, 31 are replaced by a stretchable fabric section 50, 51 and 52, 53 which overlie the knee and ankle bones or malleoli, respectively, and which have stretch capabilities in all directions such as the material used in feminine girdles and the like and known as "spandex". It is secured to the shell 20 by suitable means such as rivets 54. These areas 50 and 52 as shown in FIG. 4, for example, project from above to a short distance below the knee and ankle, respectively, thereby accommodating the knee, the malleoli and the entire anterior part of the ankle and allowing for swelling of such areas which usually occurs very shortly after an injury has been sustained. Again, as shown in FIG. 4, the two flexible elements 50, 51 and 52, 53 do not overlap but are spaced by a small gap the size of which varies in accordance with the variable contour of the knee and ankle areas.

Foot portions of the side members are shown at 60, 61, of substantially the same construction as side members 30, 31 and are likewise spaced from each other thus leaving an open gap 63 which is thus continuous from the top of the shell 20 and including gap 43 to the toe area of the cast. These foot elements are secured to the cast 20 by similar rivets 62. Preferably an arch support 65, similar to the conventional transverse arch support used in footwear, is incorporated in the foam rubber lining of the foot portions of the shell.

The cast in its preferred form likewise incorporates a tongue member 70 which is formed with an interior of wire mesh 71 of hardware cloth and the like in its upper and lower portions, similar in all respects to the wire material 33 used in members 30 and 31 and in foot members 60, 61. This wire mesh is enclosed in fabric 74, 75, corresponding to the fabric covers 34, 35 so that the tongue provides a neat and attractive cosmetic appearance when in use on the patient.

In the areas immediately overlying the knee and the ankle there is a fabric section 80 which is formed of two-way stretch material, i.e., stretchable in the direction of the length of the foot but non-stretchable in the crosswise direction. Material 80 is suitably stitched to the adjacent ends of tongue members 72 and 73, respectively, as shown.

A central strip 85 preferably of aluminum over which there is placed a pad of foam rubber 86 is enclosed in the covering of the tongue and extends throughout its entire length, being located substantially centrally thereof. The strip is for reinforcing and stiffening purposes and is bendable to conform the tongue to the shape of the foot, ankle and knee, including reshaping thereof as the swelling in the ankle and other areas diminishes. Another purpose of the strip 85 is to assure that the tongue will not crease or fold on itself, but will maintain a smooth inner surface and an attractive outer face as well, the rubber pad 86 avoiding any stress application to the skin.

A series of D-shaped fabric loops 88 are secured in spaced relation to the opposite sides of the upper portion 72 of the tongue 70 by suitable tabs 89 stitched to the face 75 of the tongue in which there are received metal D-rings 90. Similar D-shaped loops 92 are stitched to the fabric section over the calf and ankle areas and another group of D-shaped loops 94 are secured to opposite sides of the lower or foot portion of the tongue 70 with corresponding D-rings 95 in each group.

In the knee area there should be a fabric loop 96 around the posterior portion with attaching D-rings 97. A pair of straps 98 are fastened by stitching to the elastic 80 to more efficiently contour the patella or knee-cap.

Attached to the posterior face of the shell 20 is a self-adhering fabric strip 100 which extends down to and around the posterior portion of the heel and on the underside of foot portion 22 of the shell. In place of a continuous strip 100, a series of spaced lengths of this material may be secured in predetermined positions in the proper locations for use with the straps hereinafter described. This material is preferably that known in the trade as "Velcro", and the portion 100 is preferably a female type of such material and will be so described hereinafter although it is to be understood that the terms male and female as applied to such elements are relative only and that either type may be used in conjunction with the other type to achieve the desired fastening effect.

A series of fabric straps 110 are provided in order to secure the various components of the cast with the leg and foot in position. These straps comprise a first group 110 on each side which are adapted to be received through D-rings 90 of the tongue. The terminal portion of each strap 110 has a female fastener section 112 and spaced therefrom are male fastener sections 113 on its outer face as well as a male fastener section 114 on its inner face for fastening the individual straps to strip 100. Similarly, straps 120 are adapted to be received through D-rings 94 and are provided with female fasteners 122, male fasteners 123 on their outer sides, and a male fastener 124 on the opposite side and centrally of the length thereof but are located clear of the malleoli.

Another series of straps 130 are located in the foot area 22 to be received in D-rings 97 and are provided with female fasteners 132 and male fasteners 133 on their outside and with a male fastener 134 on their inner faces.

To assemble the cast in place, the foam liner 40 is first placed in shell 20 and the leg and foot of the patient located in the position shown in the various figures of the drawing. The sides of the shell 25, 26 are molded to conform to the leg and foot of the patient and the side members 30, 31 and the sides 60 and 61 of the foot are then pressed into position against the foot of the patient. During this operation the knee and ankle areas 50, 51 and 52, 53 are not subject to material pressure but are free to conform regardless of the condition of the knee and ankle as to swelling or the like.

The next step involves the placement of the tongue 70 in overlapping relation with the side elements 30, 31, 50, 51 and 60, 61. It likewise is molded manually to conform as closely as possible to the actual shape of the individual patient's thigh, knee, leg, ankle and foot.

The next step is to apply the straps by first attaching the straps in proper spaced relation along the fabric fastening strip 100 in the manner and relative position shown in FIG. 4.

In the next operation the straps are extended through the D-rings 90, 94, 97, respectively, and then folded back upon themselves so that their respective female sections 112, 122 and 132 will be received upon and secure themselves to the respective male fasteners 113, 123 and 133. In this position the parts are essentially as shown in FIG. 1 with the entire lower leg and foot of the patient engaged and encased in immobile relation to the cast. After a first application, it is usually found desirable to separate each pair of straps and to tighten the same one by one to thereby secure more firmly the entire leg in proper relation to the cast.

It thus follows that the invention provides an effective cast which affords the same degree of complete immobilization of the lower extremity as if it were protected by the usual plaster of paris cast. At the same time it is much lighter in weight than would otherwise be the case with the normal plaster of paris cast.

Another important aspect of the invention is that it is entirely possible and practical for the patient, subject to the instructions of the physician, to unfasten the straps, separate the tongue, and step out of the cast without placing weight on the foot, to enable the patient to take a bath whenever such limited degree of movement is permitted by the physician. Following a bath, the patient himself will have no difficulty in replacing his limb in the cast, and refastening the tongue with the same degree of security as when first applied by the physician. At all times, it is within the normal ability of the patient to tighten all retaining straps, as whatever swelling condition may exist begins to disappear.

The invention is also adapted for use, and has advantages, with a plaster cast in place of the tongue, either temporarily or throughout the period of recovery. Some physicians will be interested in application of the posterior shell only and will use plaster of paris to complete the immobilization process. It is difficult to apply a full leg totally plaster cast and establish proper angles at the knee and ankle and at best requires the doctor and two nurses to complete the task, followed by a length of time when one must manually hold the casted extremity perfectly still until the plaster hardens enough to use pillows as support awaiting further hardening. A thick plaster cast (six layers) will require 48 hours to totally harden and if pressures or forceful bending occurs before this—the cast will break.

With use of this invention's posterior shell, as shown in FIG. 12, a physician not desiring use of the tongue would simply pad the anterior space between the lateral panels of this pre-formed cast and proceed to apply plaster as a wrapping 140 in routine manner from the toes up to mid-thigh where the shell ends. One aide could assist the physician, probably two thickness of plaster (circular) would be adequate for immobilization and the cast would dry quicker, be lighter in weight, and in this usage would not lend to patient-tampering which at times is very desirable. At an appropriate later date, the plaster could be removed and immediately the "used" plastic posterior shell could be combined with the plastic tongue, fastened together with velcro—thereby lending the user the full benefit of the aforementioned intent of this invention.

The invention thus incorporates a highly useful and adaptable orthopedic device which can be used under the direction of the physician and in conformance with his individual preferences while assuring the fact that the overall weight and cumbersomeness of the cast are greatly reduced, for example, to a third or less. And where the full advantages of the invention are utilized the patient may readjust the cast from time to time as the swelling diminishes and may also remove the cast for purposes of bathing or the like with the assurance that he can replace it in its fully protective position as effectively as if the latter were done by the physician himself.

While the forms of apparatus herein described constitute preferred embodiments of the invention, it is to be understood that the invention is not limited to those precise forms of apparatus, and that changes may be made therein without departing from the scope of the invention which is defined in the appended claims.

What is claimed is:

1. A non-weight bearing above-the-knee cast comprising a posterior shell of rigid non-bendable material having a contoured shape to receive approximately the posterior third of the leg and foot, said shell extending from the mid-thigh distally to the knee, the lower leg, the ankle and the foot beyond the toes, said shell having a shape to support the leg in a position of physiological rest at an angle of approximately 15° to 20° to the thigh and with the foot at an angle of approximately 90° to the long axis of the lower leg, said shell having pliable fabric sides extending from the thigh distally to beyond the toes, elastic elements in said sides overlying the areas of the knee and the ankles to accommodate swelling in said areas, and means for confining the pliable sides of the elastic elements to retain the entire leg in immobilized position relative to said cast.

2. A cast as defined in claim 1 in which the adjacent edges of said sides and said elastic elements are separated by a gap, and flexible means for closing said gap.

3. A cast as defined in claim 1 in which said confining means includes a plurality of spaced straps.

4. A cast as defined in claim 1 in which said shell is enclosed in plaster from the toes to the mid-thigh.

5. A cast as defined in claim 2 in which said flexible means includes fabric means in the area of the knee and ankle bones which can stretch in two directions.

6. A cast as defined in claim 2 in which said flexible means includes a tongue of wire mesh enclosed in a fabric cover.

7. A cast as defined in claim 6 in which said tongue includes a lightweight bendable reinforcing strip.

8. A non-weight bearing above-the-kne cast, comprising a posterior shell of rigid non-bendable material having a contoured shape to receive approximately the posterior third of the leg and foot, said shell extending from the mid-thigh distally to the knee, the lower leg, the ankle, and underlying the foot, said shell having means thereon forming a pair of side extensions, said side extensions being moldable and conformable by manual pressure to the sides of the leg and foot and defining an anterior gap therebetween, said side extensions further having means therein defining elastic elements overlying the areas of the knee and ankle to accommodate swelling in these areas, and bendable tongue means attachable to said shell side extensions for closing said gap and retaining the leg in an immobilized position relative to said cast.

9. The cast as defined in claim 8 further comprising elastic sections in said tongue means in the areas of said knee and ankle bones, which elastic sections are capable of stretching in the direction of the length of the leg and foot but are essentially non-stretchable in the crosswise direction.

10. The cast of claim 8 in which said shell is formed with a shape to support the leg in a position of physiological rest at an angle of approximately 15° to 20° to the thigh and with the foot at an angle of approximately 90° to the long axis of the lower leg.

11. The cast of claim 8 further comprising a plastic foam liner received against the inner face of said shell and continuing over the heel and foot portions thereof so that the entire lower posterior extremity of the leg and foot rests in contact with the liner.

12. The cast of claim 11 in which said liner has incorporated therein means defining a transverse arch support at the foot portion of the shell.

13. A non-weight bearing above-the-knee cast comprising a rigid posterior shell having a contoured shape to receive approximately the posterior third of the leg and the foot, said shell extending from the mid-thigh distally to the knee, the lower leg, the ankle, and in underlying relation to the foot and terminating beyond the toes, said shell being formed with a shape to support the leg in a position of physiological rest at an angle of approximately 15° to 20° to the thigh and with the foot at an angle of approximately 90° to the long axis of the lower leg, said shell being further provided with a pair of side extensions which extend along the full length of the shell in the direction of the legs, and which define a gap therebetween, said side extensions overlying the lateral portions of the leg and foot and being moldable by manual pressure over the anterior portions of the upper leg and the calf to conform generally to the shape of the leg, said side extensions further having means therein defining elastically stretchable sections in the areas overlying the knee and the ankle to accommodate swelling in these areas, and means for confining the side extensions to retain the leg in an immobilized position relative to the cast.

* * * * *